United States Patent [19]

Van Koten et al.

[11] Patent Number: 4,898,955

[45] Date of Patent: Feb. 6, 1990

[54] METAL-CONTAINING ENOLATE COMPOUNDS

[75] Inventors: Gerard Van Koten, Den Dolder; Frederick H. Van Der Steen, Utrecht; Johann T. B. H. Jastrzebski, De Bilt, all of Netherlands

[73] Assignee: Gist-Brocades N.V., Delft, Netherlands

[21] Appl. No.: 283,194

[22] Filed: Dec. 12, 1988

Related U.S. Application Data

[62] Division of Ser. No. 151,816, Feb. 3, 1988.

[30] Foreign Application Priority Data

Feb. 6, 1987 [EP] European Pat. Off. ....... 87-200185.4

[51] Int. Cl.$^4$ ............................ C07F 3/06; C07F 5/06; C07F 7/10; C07F 5/02
[52] U.S. Cl. ...................................... 556/12; 556/122; 556/52; 556/403; 556/88; 556/175; 568/6
[58] Field of Search .................. 556/122, 127, 12, 52, 556/402, 403, 88, 89, 173, 175; 568/6

[56] References Cited

FOREIGN PATENT DOCUMENTS

0180398 10/1985 European Pat. Off. .
1205982 9/1970 United Kingdom .................. 556/88

OTHER PUBLICATIONS

N. Oguni et al, Chem. Abs., vol. 106, No. 19, May 11th, 1987, p. 655.
Wang et al, Chem. Abs., vol. 105, No. 25, Dec. 22nd, 1986, p. 746, The Regents of the Univ. of Calif.
Van Vliet et al, Journal of Organometallic Chem., vol. 251, 1983, pp. C-17-C-21.
J. Moskal et al; Recueil des Traviaux Chemiques des Pays-Bas, vol. 106, No. 5, May 1987, pp. C-137-131.

*Primary Examiner*—John Doll
*Assistant Examiner*—Stuart L. Hendrickson
*Attorney, Agent, or Firm*—Bierman and Muserlian

[57] ABSTRACT

Trans-β-lactams are prepared in a nearly quantitative yield by a condensation reaction of a new intermediate metal enolate and an appropriate imine. Certain new metal enolates are provided as intermediates.

3 Claims, No Drawings

METAL-CONTAINING ENOLATE COMPOUNDS

This is a division of Ser. No. 151,816 filed Feb. 3, 1988.

The present invention relates to new enolate intermediates.

This invention relates to a process for the preparation of a trans-β-lactam compound of formula I

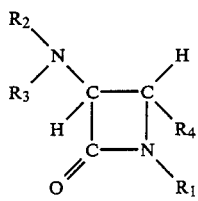

wherein $R_2$ and $R_3$ is each hydrogen, alkyl, aryl or aralkyl, each optionally substituted with alkyl, aryl or aralkyl, or is

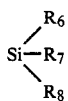

where $R_6$, $R_7$ and $R_8$ is each alkyl, aryl, aralkyl, each optionally substituted and $R_6$, $R_7$ and $R_8$ are the same or different, and $R_2$, $R_3$ are the same or different and $R_2$ and $R_3$ are not both methyl or benzyl, or $R_2$, $R_3$ together with the nitrogen atom to which they are attached form a ring with up to 8 ring atoms, each optionally substituted with alkyl, aryl or aralkyl, $R_1$ is hydrogen, halogen, alkyl, alkenyl, alkoxy, aryl or aralkyl, or is

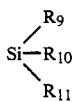

where $R_9$, $R_{10}$ and $R_{11}$ is each alkyl, aryl, aralkyl, each optionally substituted, and $R_9$, $R_{10}$ and $R_{11}$ are the same or different, $R_4$ is alkyl, hydroxy, halogen, sulphonyl, alkoxy, alkenyl, alkynyl or aryl, each optionally substituted, or is

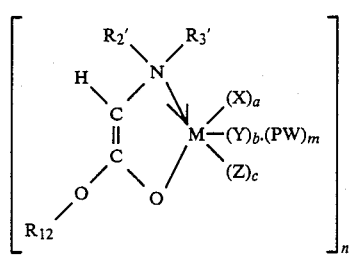

where $R_5$ is alkyl.

This invention relates also to new metal compounds of formula II

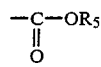

wherein $R_2'$ and $R_3'$ is $R_2$ and $R_3$ except of both being hydrogen, $R_{12}$ is alkyl, aryl or aralkyl, each optionally substituted with alkyl, aryl or aralkyl, M is zinc, aluminum, zirconium, borium, tin or titanium, P is an alkali metal, W, X, Y and Z is alkyl, aryl, halide, alkoxide, thiolate, triflate or any other substituted sulphonate or any other suitable anionic group, and W, X, Y and Z are the same or different and a, b, c and m=0–1, n=1–6, all being integers.

This invention relates also to a process for the preparation of S-trans-β-lactams of formula Ia

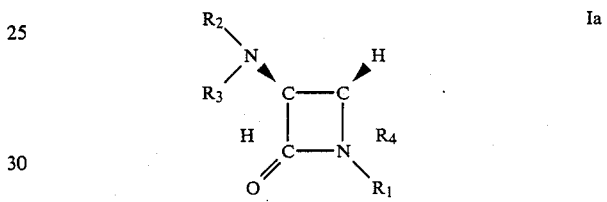

wherein $R_1$, $R_2$, $R_3$ and $R_4$ are as defined above.

Many research efforts have been expended to discover or synthesize new β-lactams and to develope new methods to synthesize known β-lactams (2-azetidinones). This is because these compounds are potent antibiotics, very well tolerated by human beings. The β-lactams obtained are four-membered cyclic amides, the principle building blocks of penicillins and cephalosporins.

Developing a method for synthesizing interesting 1,2-diaminoethanes, 1-amino-2-imino-ethanes, α-hydroxy-imines and related organic compounds (M. R. P. van Vliet, G. van Koten, J. T. B. H. Jastrzebski, K. Vrieze and A. L. Spek, J. Organometal, Chem., 251, C17 (1983); M. R. P. van Vliet, Ph.D. Thesis, Amsterdam (1987); M. R. P. van Vliet, G. van Koten, P. Buysingh, J. T. B. H. Jastrzebski and A. L. Spek, Organometallics, 6, 537 (1987)), metal precursor complexes were formed whereby ZnWX and AlWXY were involved.

Embroidering on this the synthesis of trans-β-lactams from the metal complexes formed between the α-iminoesters $R_a$—N=C(H)C(O$R_b$)=O (where $R_a$ is alkyl, $R_b$ is alkyl) and diethylzinc, was found, as depicted in scheme I.

scheme I

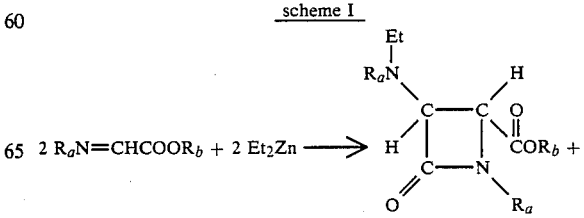

-continued
scheme I

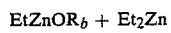

The trans-geometry of the β-lactams formed is unambigously confirmed by an X-ray crystal structure determination of the β-lactam compound in which $R_a$ is t-butyl and $R_b$ is methyl (M. R. P. van Vliet, J. T. B. H. Jastrzebski, W. J. Klaver, K. Goubitz and G. van Koten, Recl. Trav. Chim. Pays-Bas, 100, 137 (1987)). A serious disadvantage of this β-lactam preparation is that only a small variation in substituents is possible, only with $R_a$ is t-butyl or i-propyl and $R_b$ is methyl or ethyl is a β-lactam formed. Moreover, only with primary dialkyl zinc compounds a β-lactam is formed.

Recent reinvestigations of the reaction depicted in scheme I revealed that firstly an organozinc complex is formed which is probably converted into a zinc enolate, which in a subsequent reaction with a second equivalent of the iminoester is converted into the trans-β-lactam species (see scheme II).

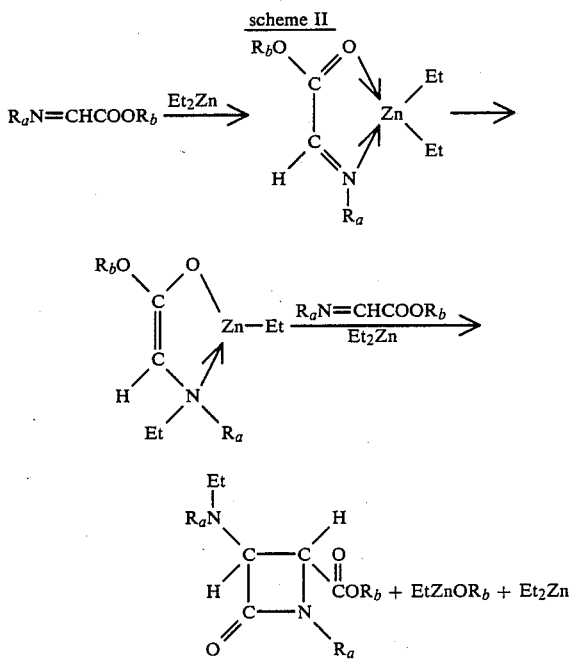

A zinc enolate compound has been isolated of which the structure in the solid was confirmed by an X-ray determination.

The recent reinvestigations showed that the supposed intermediate zinc enolate (see scheme II) and other metal enolates could be prepared in situ via another route by the reaction of am alkali metal enolate with a suitable metal compound. This reaction has been depicted in scheme III, all variable substituents are as defined above.

scheme III

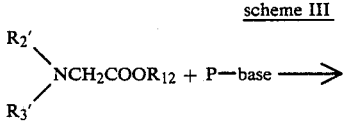

-continued
scheme III

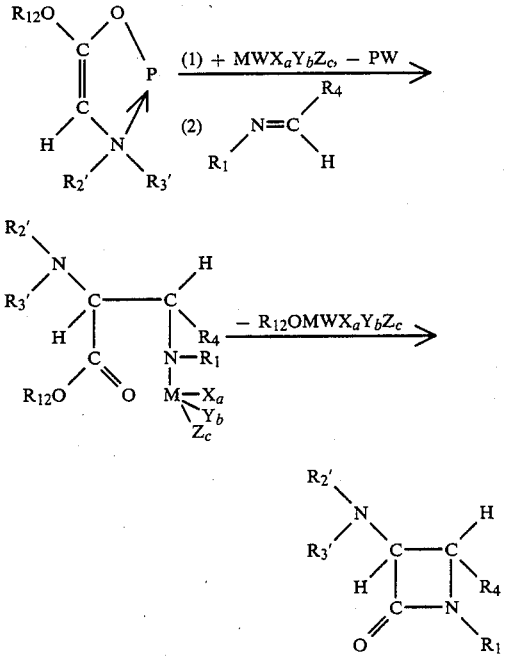

The metal enolates so obtained show a unique reactivity in that, in reaction with appropiate imine substrates they afford exclusively the trans-β-lactams in quantitative yields. This novel reactivity is surprising because the present routes involving enolates yielded only cis-β-lactams or a mixture of cis- and trans-β-lactams.

Many syntheses of β-lactams are known, see for instance a comprehensive review of the various syntheses of β-lactams in "The Chemistry of Heterocycles", Part 2, chapter II, The synthesis of the β-lactam Function by G. A. Koppel, edited by John Wiley and Sons (1983). However, there are no routes described to synthesize trans-β-lactams with 1-H (-or hydrolysable group), 3-$NH_2$ and 4-alkyl substituents by aldolcondensation followed by ringclosure.

P. Andreoli, G. Gainelli, M. Contento, D. Giacomini, G. Martelli and M. Panunzio report in Tetrahedron Lett., 27(15), 1695–1698 (1986) the reaction of nitriles with glycinate esters in the presence of a lithium compound and trimethylchlorosilane. However, the isolated 3,4-disubstituted azetidinones have mainly the cis-configuration.

The synthesis of 4-unsubstituted β-lactams from formaldehyde imines, formed in situ from nitriles and glycinate esters, has been described in European patent application No. 180398.

N-unsubstituted 2-azetidinones have been prepared from N-trimethylsilyl aldimines and ester enolates in the presence of lithium diisopropylamide (D. J. Hart, K. Kanai, D. G. Thomas and T. K. Yang, J. Amer. Chem. Soc., 48, 289 (1983). These 2-azetidinones do not have a (substituted) nitrogen atom at the 3-position.

The present invention comprises the unexpected, easy and selective synthesis of 1,3,4-trisubstituted trans-2-azetidinones in which the atom linked to the C-3 carbon atom is nitrogen and in which, if necessary, the substituent at the 1-position can easily be removed by hydrolysis. The target compounds containing at least 90% of the trans configuration have been obtained from a condensation reaction of a new intermediate amino metal enolate and an appropiate imine in a nearly quantitative yield. This is in no way described or taught in the literature.

Also a way has been found to synthesize one stereospecific enantiomer in significant excess. It is possible to synthezise an enantiomerically enriched trans-$\beta$-lactam enantiomer by choosing the suitable enantiomer of the glycine alkyl ester as a starting material. Suitable means here the glycine alkyl ester enantiomer that is appropiate to prepare the desired trans-$\beta$-lactam enantiomer.

It is an object of the invention to provide a process for the preparation of a trans-$\beta$-lactam of formula I wherein $R_1$, $R_2$, $R_3$, $R_4$ are as defined above, characterized in that a compound of formula II

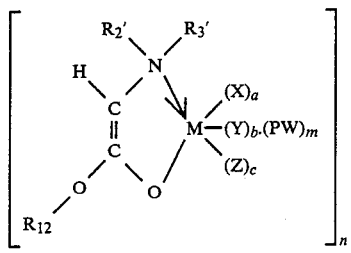

wherein
$R_{12}$, M, P, W, X, Y, R, a, b, c, m and n are as defined above, $R_2'$ and $R_3'$ is $R_2$ and $R_3$ respectively with the proviso that when $R_2$ and $R_3$ is hydrogen $R_2'$ and $R_3'$ together with the nitrogen atom to which they are attached form a ring of formula III

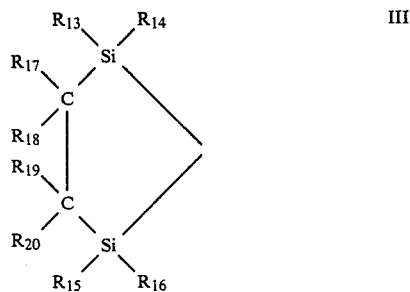

wherein
$R_{13}$, $R_{14}$, $R_{15}$, $R_{16}$, $R_{17}$, $R_{18}$, $R_{19}$ and $R_{20}$ is each alkyl, aryl, aralkyl and $R_{13}$, $R_{14}$, $R_{15}$, $R_{16}$, $R_{17}$,
$R_{18}$, $R_{19}$ and $R_{20}$ are the same or different,
is reacted with an imine of formula IV

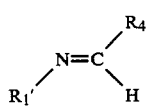

where $R_4$ is as defined above and $R_1'$ is $R_1$, with the proviso that when $R_1$ is hydrogen, $R_1'$ is

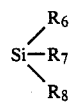

where
$R_6$, $R_7$ and $R_8$ are as above defined, which group is hydrolysed after the reaction by acid or base, and with the proviso that when $R_2$ and $R_3$ are both hydrogen, the ring of formula III is removed after the reaction by acid or base catalyzed hydrolysis.

In another object of the invention compounds are provided of formula II, depicted above, wherein
$R_2'$ and $R_3'$ are $R_2$ and $R_3$, respectively, except of both being hydrogen, and
$R_{12}$, M, P, W, X, Y, Z, a, b, c, m and n are defined as above.

Furthermore, the invention provides a process for the preparation of compounds of formula II, as defined above, characterized by the reaction of a $R_2'R_3'$N-glycine alkyl ester with an alkali metal base and a metal compound with the formula $MW(X)_a(Y)_b(Z)_c$ where $R_2'$, $R_3'$, M, W, X, Y, Z, a, b, c, m and n are as defined just above.

The invention also provides a one-pot process for the preparation of trans-$\beta$-lactams of formula I, as defined above, characterized by the conversion of a $R_2'R_3'$N-glycine alkyl ester where $R_2'$ and $R_3'$ are as defined on page 7, with an imine of formula IV as defined above, in the presence of an alkali metal base and a metal compound of formula $MW(X)_a(Y)_b(Z)_c$ where M, W, X, Y, Z, a, b and c are as defined above, with the proviso that when $R_2$, $R_3$ is hydrogen the ring of formula III is removed after the reaction by acid or base catalyzed hydrolysis.

Finally, the invention provides a process for the preparation of a (3S)-trans-$\beta$-lactam of formula Ia wherein $R_1$, $R_2$, $R_3$ and $R_4$ are as defined above, characterized by the conversion of the suitable enantiomer of the $R_2'R_3'$N-glycine alkyl ester, with $R_2'$ and $R_3'$ are as defined on page 7, with the proviso that when $R_2'$ and $R_3'$ are both hydrogen, the ring of formula III is removed after the reaction by acid or base catalyzed hydrolysis.

Preferably, the alkali metal base used is lithium diisopropylamide or sodium hexamethyldisilazane. Preferably, M in the metal compound $MW(X)_a(Y)_b(Z)_c$ is zinc or aluminum. The values of a, b and c depend on the valency of M.

It is certainly possible to carry out the synthesis of trans-$\beta$-lactams as a "one-pot" process. For instance, first of all lithium diisopropylamide is generated by adding one equivalent n-butyllithium in n-hexane to a solution of diisopropylamine in benzene at room temperature, followed by the addition of $Et_2NCH_2COOEt$. The resulting lithium enolate partly crystallizes during the reaction. Then one equivalent of dry zinc dichloride is added (a clear solution is now obtained) and finally one equivalent of N-(benzylidene)methylamine is added and the reaction mixture is generally refluxed for half an hour. According to this procedure a variety of trans-$\beta$-lactams can be synthesized using the appropiate imines. However, if no metal compound ($MW(X)_a(Y)_b(Z)_c$ with M, P, W, X, Y, Z, a, b and c are as defined above) is added, no $\beta$-lactam is formed.

It is also possible to synthesize an enantiomerically enriched trans-$\beta$-lactam from a suitable enantiomerically pure glycine alkyl ester and an appropiate imine. For instance, reaction of the pure (−)methyl ester of N,N-diethylglycine with N-methylbenzaldimine afforded the trans-$\beta$-lactam in a quantitative yield. $^1$H NMR experiments of this compound in $CDCl_3$ with optically active paramagnetic shift reagents show the presence of two enantiomers in a 1:2 molar ratio, thus indicating an enantiomeric excess of 33%.

All these reactions are preferably carried out in inert, apolar or weakly polar solvents as for instance pentane, benzene and diethyl ether. Furthermore, it is very important that the metal compounds (with the formula $MW(X)_a(Y)_b(Z)_c$ where M, P, W, X, Y, Z, a, b and c are defined as above) used in these reactions essentially are free of water. When small amounts of water are present, lower yields are obtained and the stereo-selectivity decreases.

The following non-limitative examples illustrate the present invention.

GENERAL PROCEDURE

All reactions were carried out in an atmosphere of dry nitrogen using standard Schlenk-techniques (Manipulations of air-sensitive compounds, D. F. Shriver, editor Mc. Graw Hill, N.Y., 1969). Solvents were distilled from sodium prior to use. N-t-butyliminoethylglyoxylate and N-i-propyliminomethylglyoxylate were prepared in a condensation reaction; cf. t-butylamine and i-propylamine with ethylglyoxylate and methylglyoxylate respectively. 2,2,5,5-tetramethyl-1-aza-2,5-disilylacyclopentane-1-acetic acid ethyl ester has been described in Tetrahedron Lett., 22, 1787 (1981). Solutions of n-butyllithium in n-hexane and diethylzinc in n-hexane are commercially available.

It is very important to use a dry metal compound to prepare the metal enolates. Therefore for instance zinc dichloride was either prepared from zinc and dry hydrogen chloride in diethyl ether or commercially available zinc dichloride was dehydrated in refluxing thionyl chloride.

EXAMPLE I

Synthesis of the ethylzinc enolate lithium chloride complex of N,N-diethylglycine ethyl ester To a solution containing 2.02 g (20 mmoles) of diisopropylamine in 30 ml diethyl ether, 13.33 ml (1.5 molar) n-butyllithium in hexane, equivalent to 20 mmoles n-butyllithium, was added at 0° C. The temperature of the reaction mixture was raised to room temperature and stirred for 10 minutes. To a stirred solution of the resulting lithium diisopropylamide 3.18 g (20 millimole) of N,N-diethylglycine ethyl ester was added so as to form immediately a white suspension of the lithium enolate of N,N-diethylglycine ethyl ester. The reaction mixture was stirred for 30 minutes and then cooled to −35° C. At this temperature, a solution containing 2.6 g (20 mmoles) of ethylzinc chloride in 15 ml diethyl ether was added with stirring, resulting in formation of a heavy precipitate in a colourless solution. This reaction mixture was stirred for 30 min at −35° C., the temperature was then raised to 25° C. and stirring was continued for another 30 min.

The solution was then decanted from the precipitate which was washed three times with 15 ml portions of n-pentane. Finally the product was dried in vacuo at 25° C. The yield was 4.5 g (76.3%) of the ethylzinc enolate lithium chloride complex of N,N-diethylglycine ethyl ester as an air sensitive white solid with the properties: $^1$H NMR (60 MHz, $C_6D_6$): $\delta$3.70 (s, 1H, C=CH), 3.60 (m, 2H, $OCH_2CH_3$), 2.65 (m, 4H, $NCH_2CH_3$), 1.55 (t, 3H, $ZnCH_2CH_3$), 1.15 (m, 9H, $CH_2CH_3$ and $OCH_2CH_3$), 0.50 (m, 2H, $ZnCH_2CH_3$).

Analyses found: C 40.56; H 7.58; N 4.65; Zn 22.09. Analyses calculated for $C_{10}H_{21}NO_2ZnLiCl$: C 40.70; H 7.17; N 4.74; Zn 22.16.

EXAMPLE II

Synthesis of 1-methyl-3-substituted-4-phenyl-2-azetidinone

A. Synthesis of trans-1-methyl-3-diethylamino-4-phenyl-2-azetidinone 2.95 g (10 mmoles) of the ethylzinc enolate lithium chloride complex of N,N-diethylglycine ethyl ester (the product obtained from example I) was dissolved in 20 ml benzene at room temperature. To this clear colourless solution was added 1.19 g (10 mmoles) of N-(benzylidene)methylamine. The resulting solution was refluxed for 30 min. During this period some precipitate formed. The reaction mixture was cooled to room temperature and diluted with 25 ml diethyl ether. To this mixture, 10 ml of a saturated aqueous ammonium-chloride solution was added. The aqueous layer was separated and the organic layer was twice washed with 10 ml of an aqueous ammonium chloride solution and twice with 10 ml portions of water, dried over sodium sulfate and concentrated in vacuo yielding 2.2 g (95%) of the 2-azetidinone product as a white solid with the properties: m.p. 70°–71° C. $^1$H NMR (60 MHz, $CDCl_3$): $\delta$7.30 (m, 5H, arom.), 4.60 (d, J=1.6 Hz, 1H, NCHCHPh), 4.10 (d, J=1.6 Hz, 1H, NCHCHPh), 2.90 (s, 3H, $NCH_3$), 2.90 (q, 4H, $NCH_2CH_3$), 1.15 (t, 6H, $NCH_2CH_3$).

Analyses found: C 72.13; H 8.80; N 11.73. Analyses calculated for $C_{14}H_{20}N_2O$: C 72.38; H 8.68; N 12.06.

B. Synthesis of 1-methyl-3-methylphenylamino-4-phenyl-2-azetidinone 10 mmoles of n-butyllithium (6.67 ml of a 1.5 molar solution in hexane) was added to a stirred solution containing diisopropylamine (1.40 ml; 10 mmoles) and 25 ml benzene at room temperature. This reaction mixture was stirred for 15 min. Then N,N-methylphenylglycine ethyl ester (1.93 g; 10 mmoles) was added. The solution was stirred for another 10 min. Then 10 mmoles of zinc dichloride (10.00 ml of a 1.0 molar solution in diethyl ether) was added. After stirring of another 10 min, N-(benzylidene)methylamine (1.19 g; 10 mmoles) was added and the reaction mixture was refluxed for 25 hours. The reaction mixture was poured into 20 ml of a saturated aqueous ammonium chloride solution. The water layer was extracted with diethyl ether. The organic extract was dried with magnesium sulfate and concentrated in vacuo yielding 2.50 g (94%) of the 2-azetidinone product as a pale brown solid. The 60 MHz $^1$H NMR-spectrum revealed that the product was a mixture of cis- and trans-isomers (cis/trans ratio 2:98).

Recrystallisation from diethyl ether afforded the pure 2-azetidinone products as pale yellow (trans-isomer) and brown (cis-isomer) crystals which could be separated by crystal-picking. Properties of the trans-isomer): m.p. 84° C. $^1$H NMR ($CDCl_3$): $\delta$7.44 (m, 3H, ArH), 7.30 (m, 2H, ArH), 7.12 (t, J=7.0 Hz, 2H, ArH), 6.76 (t, J=7.0 Hz, 1H, ArH), 6.56 (d, J=7.7 Hz, 2H, ArH), 4.75 (br. s, 1H, N—CH—CH—Ph), 4.50 (d, J=2.2 Hz, 1H, N—CH—CH—Ph), 3.15 (s, 3H, Ph—N—$CH_3$), 2.90 (s, 3H, N—$CH_3$). 13 C NMR ($CDCl_3$): $\delta$167.76 (C=O), 149.26, 137.12, 129.75, 129.64, 129.20, 126.86, 119.22, 114.91 (ArC), 78.35 (N—CH—CH—Ph), 63.51 (N—CH—CH—Ph), 35.42 (Ph—N—CH₃), 27.35 (N—CH₃). IR (KBr): 1760 cm⁻¹.

Properties of the cis-isomer: m.p. 137° C. ¹H NMR (CDCl₃): δ6.40–7.44 (m, 10H, ArH), 5.10 (d, J=4.4 Hz, 1H, N—CH—CH—Ph), 4.77 (d, J=4.4 Hz, 1H, N—CH—CH—Ph), 3.18 (s, 3H, Ph—N—CH₃), 2.70 (s, 3H, N—CH₃). IR (KBr): 1748 cm⁻¹.

EXAMPLE III

Synthesis of trans-1-(substituted)-3-diethylamino-4-phenyl-2-azetidinone (one-pot process)

A. Synthesis of trans-1-methyl-3-diethylamino-4-phenyl-2-azetidinone 13.33 ml (1.5 molar) of n-butyllithium in hexane, equivalent to 20 mmoles n-butyllithium was added to a solution of 2.02 g (20 mmoles) of diisopropylamine in 25 ml benzene. The resulting solution of lithium diisopropylamide so obtained was stirred for 10 min. Then 3.18 g (20 mmoles) of N,N-diethylglycine ethyl ester was added giving an immediate white suspension. This suspension was stirred for 30 min. Then a solution of 2.73 g (20 mmoles) of zinc dichloride in 20 ml diethyl ether was added resulting in a yellow solution and this solution was stirred for another 10 min. Most of the diethyl ether and hexane present in solution was evaporated in vacuo. 2.38 g (20 mmoles) of N-(benzylidene)-methylamine was added to the resulting benzene solution and the reaction mixture refluxed for 30 min. During this period some solid material precipitated. The reaction mixture was cooled down to room temperature and diluted with 20 ml of diethyl ether. 15 ml of a saturated aqueous ammonium chloride solution was added to the reaction mixture. The organic phase was separated and was washed twice with 15 ml portions of a saturated aqueous ammonium chloride solution and twice with 15 ml portions of water, dried with sodium sulfate and concentrated in vacuo yielding 4.2 g (90.5%) of the trans-2-azetidinone product as a white solid with the same properties as those given for the product in example 1.

B. Table I shows the synthetic scheme for this 2-azetidinone and another representative example.

TABLE I

Et₂NCH₂COOEt $\xrightarrow[\text{(3) R}_4\text{—C(H)=N—R}_1]{\text{(1) LDA, (2) ZnCl}_2}$

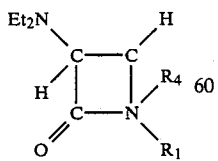

| | yield | cis | trans |
|---|---|---|---|
| 1 R₁ = methyl; R₄ = phenyl | 90% | <2% | >98% |
| 2 R₁ = benzyl; R₄ = phenyl | 92% | <2% | >98% |

EXAMPLE IV

Synthesis of trans-3-methylphenylamino-4-([trimethylsilyl]ethynyl)-2-azetidinone 10 mmoles of n-butyllithium (6.67 ml of a 1.5 molar solution in hexane) was added to a stirred solution containing diisopropylamine (1.40 ml; 10 mmoles) and 25 ml benzene at room temperature. This reaction mixture was stirred for 15 min and then N,N-methylphenylglycine ethyl ester (1.93 g; 10 mmoles) was added. The solution was stirred for another 10 min and then 10 mmoles of zinc dichloride (10.00 ml of a 1.0 molar solution in diethyl ether) was added. The reaction mixture was stirred for another 5 min and then N-(3-trimethylsilyl-2-propynylidene)-trimethylsilylamine (1.98; 10 mmoles) was added and the reaction mixture was refluxed for 8 hours. The reaction mixture was poured into 20 ml of a saturated aqueous ammonium chloride solution. The water layer was extracted with diethyl ether. The organic extract was dried with magnesium sulfate and concentrated in vacuo yielding 2.70 g (99%) of the 2-azetidinone product as a dark-brown solid.

Recrystallisation from diethyl ether/pentane afforded the pure trans-product as off-white crystals with the properties: m.p. 136° C. ¹H NMR (CDCl₃): δ7.08 (m, 2H, ArH), 6.74 (m, 3H, ArH), 6.18 (br. s, 1H, N—H), 4.90 (br. s, 1H, N—CH—CH—C≡C), 4.03 (d, J=2.2 Hz, 1H, N—CH—CH—C≡C), 2.85 (s, 3H, N—CH₃), 0.35 (s, 9H, SiMe₃). IR (KBr): 1786 cm⁻¹.

Analyses found: C 65.59, H 7.66, N 10.21. Analyses calculated
for C₁₅H₂₀N₂OSi: C 66.13, H 7.40, N 10.28.

EXAMPLE V

Synthesis of trans-3-diethylamino-4-substituted-2-azetidinone (one-pot process)

Following the same procedure and using the same reaction conditions as used in Example III, 1-unsubstituted trans-β-lactams were obtained by carrying out the reaction with N-trimethylsilyl protected imines. Instead of N-(benzylidene)methylamine, the N-SiMe₃ group is hydrolyzed during the aqueous work up. Representative examples are given in Table II.

TABLE II

Et₂NCH₂COOEt $\xrightarrow[\text{(3) R}_4\text{—C(H)=N—SiMe}_3]{\text{(1) LDA, (2) ZnCl}_2}$

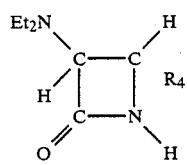

| | yield | cis | trans |
|---|---|---|---|
| 1 R₄ = phenyl | 94% | <2% | >98% |
| 2 R₄ = C≡C—Phenyl | 92% | <2% | >98% |
| 3 R₄ = C≡C—SiMe₃ | 95% | <2% | >98% |

EXAMPLE VI

Synthesis of 1-methyl-3-amino-4-phenyl-2-azetidinone

A. Synthesis of 1-methyl-3-(2,2,5,5-tetramethyl-1-aza-2,5-disilacyclopentyl)-4-phenyl-2-azetidinone 10 mmoles of n-butyllithium (6.67 ml of a 1.5 molar solution in hexane) was added to a stirred solution containing diisopropylamine (1.40 ml; 10 mmoles) and 25 ml of diethyl ether at −70° C. This reaction mixture was stirred for 10 min and then 2,2,5,5-tetramethyl-1-aza-2,5-disilacyclopentane-1-acetic acid ethyl ester (2.45 g; 10 mmoles) was added. The solution was stirred for another 15 min at −70° C. and then 10 mmoles of zinc dichloride (6.76 ml of a 1.48 molar solution in diethylether) was added. After 5 min at −70° C., a white solid (LiCl) began to precipitate. Then N-(benzylidene)-methylamine (1.19 g; 10 mmoles) was added. The reaction mixture was stirred for another 15 min at −70° C. and, after being warmed up to room temperature, quenched with 20 ml of a saturated aqueous ammonium chloride solution. The water layer was extracted with diethyl ether. The diethyl ether extract was washed with water, dried with sodium sulfate and concentrated in vacuo to give 3.05 g (96%) of the pure 2-azetidinone product as a pale yellow solid. The $^1$H NMR spectrum revealed that the product was a mixture of cis and trans isomers (cis/trans ratio 8:92).

Recrystallisation from diethyl ether/hexane gave the pure trans-product as colourless crystals with the properties: m.p. 90.5°–91.5° C. $^1$H NMR (CDCl$_3$): δ7.17–7.44 (m, 5H, ArH), 4.10 (d, J=1.8 Hz, 1H, N—CH—CH—Ph), 4.05 (m, 1H, N—CH—CH—Ph), 2.75 (br. s, 3H, N—CH$_3$), 0.63—0.85 (m, 4H, Si—CH$_2$—CH$_2$—Si), 0.12 (s, 6H, Si(CH$_3$)$_2$), 0.04 (s, 6H, Si(CH$_3$)$_2$). $^{13}$C NMR (CDCl$_3$): δ170.23 (C=O), 137.03, 128.83, 128.25, 126.18 (ArC), 72.92 (N—CH—CH—Ph), 68.63 (N—CH—CH—Ph), 26.58 (N—CH$_3$), 7.94 (Si—CH$_2$CH$_2$—Si), 0.59 (Si(CH$_3$)$_2$), 0.10 (Si(CH$_3$)$_2$).

B. Direct conversion into 1-methyl-3-amino-4-phenyl-2-azetidinone

Following the same procedure as described above up to but not including the quenching step, a reaction mixture containing 1-methyl-3-(2,2,5,5-tetramethyl-1-aza-2,5-disilacyclopentyl)-4-phenyl-2-azetidinone was prepared. The reaction mixture at room temperature was quenched with 50 ml of a 1 molar HCl solution in water. The water layer was extracted with diethyl ether and then basified with solid KOH to pH 11 and extracted with dichloromethane. The dichloromethane extract was washed with 50 ml of a saturated aqueous ammonium chloride solution, dried with sodium sulfate and concentrated in vacuo to give 1.28 g (73%) of the pure 2-azetidinone product as a pale yellow oil, which solidified upon standing. .

The $^1$H NMR spectrum revealed that the product was a mixture of cis- and trans isomers (cis/trans ratio 6:92) with the properties: IR (CDCl$_3$): 1740 cm$^{-1}$; $^1$H NMR (CDCl$_3$): δ7.18–7.44 (m, 5H, ArH), 4.19 (d, J=1.8 Hz, 1H, H$_2$N—CH—CH—Ph), 3.91 (m, 1H, H$_2$N—CH—CH—Ph), 2.76 (br. s, 3H, N—CH$_3$), 1.91 (br. s, 2H, NH$_2$), for the trans-isomer; $^1$H NMR (CDCl$_3$): δ4.75 (d, J=4.9 Hz, 1H, H$_2$N—CH—CH—Ph), 4.47 (d, J=4.9 Hz, 1H, H$_2$N—CH—CH—Ph), 2.83 (s, 3H, N—CH$_3$) for the cis-isomer. $^{13}$C NMR (CDCl$_3$): δ170.33 (C=O), 136.59, 128.67, 128.16, 125.89 (ArC), 70.23 (N—CH—CH—PH), 67.28 (N—CH—CH—Ph), 26.53 (N—CH$_3$) for the trans-isomer; $^{13}$C NMR (CDCl$_3$): δ64.60 (N—CH—CH—Ph), 63.60 (N—CH—CH—Ph) for the cis-isomer.

Pure trans-1-methyl-3-amino-4-phenyl-2-azetidinone could be obtained by starting from pure trans-1-methyl-3-(2,2,5,5-tetramethyl-1-aza-2,5-disilacyclopentyl)-4-phenyl-2-azetidinone. To a solution of the pure trans-2-azetidinone (0.80 g; 2.5 mmoles) in 20 ml of diethyl ether was added 20 ml of a 1 molar HCl solution in water at room temperature. The mixture was stirred for 1 hour, then the etheral layer was separated and thereafter the water layer was neutralized with solid KOH to pH 6 and extracted with dichloromethane.

The dichloromethane extract was dried with sodium sulfate and concentrated in vacuo to give 0.37 g (84%) of the pure trans 1-methyl-3-amino-4-phenyl-2-azetidinone as a colourless oil, which solidified upon standing; m.p. 51.5° C.

Table III shows this scheme for preparing 3-amino-substituted β-lactams and some of the intermediate β-lactams prepared, their percent yields and their physical data.

TABLE III

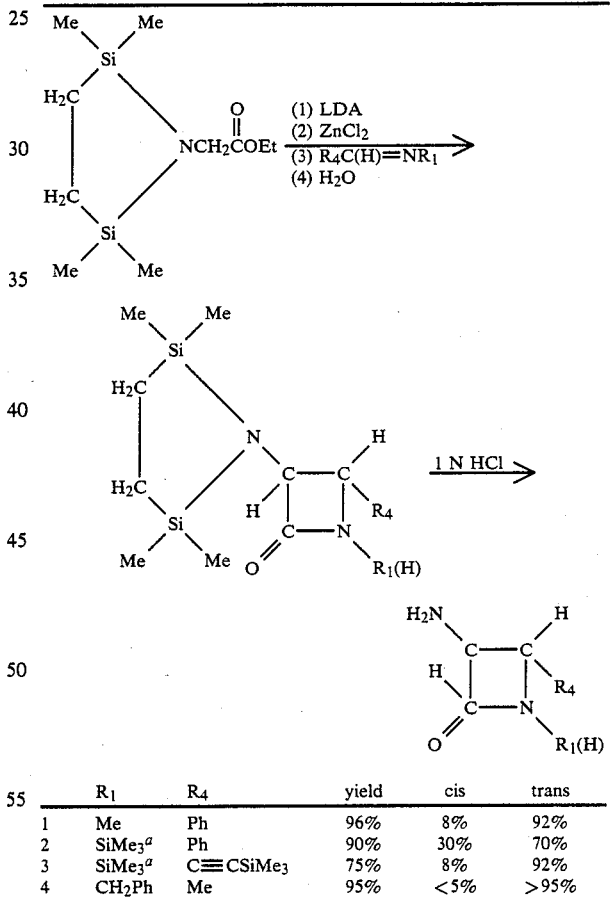

| R$_1$ | R$_4$ | yield | cis | trans |
|---|---|---|---|---|
| 1 Me | Ph | 96% | 8% | 92% |
| 2 SiMe$_3$$^a$ | Ph | 90% | 30% | 70% |
| 3 SiMe$_3$$^a$ | C≡CSiMe$_3$ | 75% | 8% | 92% |
| 4 CH$_2$Ph | Me | 95% | <5% | >95% |

$^a$upon hydrolysis the trimethylsilyl group is removed and replaced with a hydrogen.

Addendum to Table III: physical data of compounds 2, 3 and 4.

3-(2,2,5,5-tetramethyl-1-aza-2,5-disilacyclopentyl)-4-phenyl-2-azetidinone trans-isomer: pale yellow solid, m.p. 101° C. $^1$H NMR (CDCl$_3$): δ7.12 (s, 5H, ArH), 6.29 (br. s, H, NH), 4.23

(d, J=2.1 Hz, 1H, N—CH—CH—Ph), 3.92 (d, J=2.1 Hz, 1H, N—CH—CH—Ph), 0.70 (s, 4H, Si—CH$_2$—CH$_2$—Si), 0.13 (s, 6H, Si(CH$_3$)$_2$), 0.05 (s, 6H, Si(CH$_3$)$_2$).

$^{13}$C NMR (CDCl$_3$): δ171.65 (C=O), 139.34, 128.76, 128.13, 125.51 (ArC), 73.61 (N—CH—CH—Ph), 62.76 (N—CH—CH—Ph), 7.97 (Si—CH$_2$—CH$_2$—Si), 0.45 (Si(CH$_3$)$_2$).

cis-isomer: $^1$H NMR (CDCl$_3$): δ4.68 (d, J=5.3 Hz, 1H, N—CH—CH—Ph), 4.42 (d, J=5.3 Hz, 1H, N—CH—CH—Ph).

3-amino-4-phenyl-2-azetidinone trans-isomer: pale yellow solid. $^1$H NMR (CDCl$_3$): δ7.10 (s, 5H, ArH), 6.32 (br. s, 1H, NH), 4.22 (d, J=2.0 Hz, 1H, H$_2$N—CH—CH—Ph), 3.81 (d, J=2.0 Hz, 1H, H$_2$N—CH—CH—Ph), 1.62 (br. s, 2H, NH$_2$).

$^{13}$C NMR (CDCl$_3$): δ171.55 (C=O), 138.93, 128.77, 126.69, 125.46 (ArC), 71.08 (N—CH—CH—Ph), 62.70 (N—CH—CH—Ph).

IR (CDCl$_3$): 1755 cm$^{-1}$.

3-(2,2,5,5-tetramethyl-2,5-disilacyclopentyl-1-aza)-4-[(trimethylsilyl)ethynyl]-2-azetidinone trans-isomer: pale brown solid. $^1$H NMR (CDCl$_3$): δ7.25 (br. s, 1H, NH), 4.48 (d, J=2.1 Hz, 1H, N—CH—CH—C≡CSiMe$_3$), 3.61 (d, J=2.1 Hz, 1H, N—CH—CH—C CSiMe$_3$), 0.71 (s, 4H, Si—CH$_2$—CH$_2$—Si), 0.15 (br. s, 21H, Si(CH$_3$)$_2$).

1-benzyl-3-(2,2,5,5-tetramethyl-1-aza-2,5-disilacyclopentyl)-4-phenyl-2-azetidinone trans-isomer: pale yellow oil. $^1$H NMR (CDCl$_3$): δ7.13 (s, 5H, ArH), 4.59 (d, J=15 Hz, 1H, N—CH$_2$—Ph), 3.96 (d, J=15 Hz, 1H, N—CH$_2$—Ph), 3.79 (d, J=2.2 Hz, 1H, N—CH—CH—CH$_3$), 3.24 (dq, J=2.2 and J=6.0 Hz, 1H, N—CH—CH—CH$_3$), 1.32 (d, J=6.0 Hz, 3H, N—CH—CH—CH$_3$), 0.74 (s, 4H, Si—CH$_2$—CH$_2$—Si), 0.15 (s, 6H, Si(CH$_3$)$_2$), 0.09 (s, 6H, Si(CH$_3$)$_2$).

$^{13}$C NMR (CDCl$_3$): δ168.79 (C=O), 138.87, 128.40, 128.01, 127.38 (ArC), 68.46 (N—CH—CH—CH$_3$), 58.67 (N—CH—CH—CH$_3$), 43.73 (N—CH$_2$—Ph), 16.40 (N—CH—CH—CH$_3$), 7.80 (Si—CH$_2$—CH$_2$—Si), 0.32 (Si(CH$_3$)$_2$), 0.05 (Si(CH$_3$)$_2$).

EXAMPLE VII

Synthesis of 1-methyl-3-bis(trimethylsilyl)amino-4-phenyl-2-azetidinone 10 mmoles of n-butyllithium (6.67 ml of a 1.5 molar solution in hexane) was added to a stirred solution containing diisopropylamine (1.40 ml; 10 mmoles) and 25 ml of diethyl ether at −70° C. This reaction mixture was stirred for 10 min and then N,N-bis(trimethylsilyl)glycine ethyl ester (2.47 g; 10 mmoles) was added. The solution was stirred for another 10 min at −70° C. and then 10 mmoles of zinc dichloride (6.76 ml of a 1.48 molar solution in diethyl ether) was added. After 5 min at −70° C. a white solid (LiCl) began to precipitate. Then N-(benzylidine)methylamine (1.19 g; 10 mmoles) was added. The reaction mixture was stirred for another 15 min at −70° C. and after being warmed up to room temperature quenched with 20 ml of a saturated aqueous ammonium chloride solution. The water layer was extracted with diethyl ether. The diethyl ether extract was washed with water, dried with sodium sulfate and concentrated in vacuo to give 2.41 g (75%) of the trans-azetidinone product as a pale yellow oil with the properties:

$^1$H NMR (CDCl$_3$): δ7.08-7.42 (m, 5H, ArH), 4.18 (d, J=1.8 Hz, 1H, N—CH—CH—Ph), 4.09 (m, 1H, N—CH—CH—Ph), 2.73 (br. s, 3H, N—CH$_3$), 0.20 (s, 18H, Si(CH$_3$)$_3$.

$^{13}$C NMR (CDCl$_3$): δ171.57 (C=O) 136.92, 128.78, 128.11, 125.76 (ArC), 75.25 (N—CH—CH—Ph), 68.61 (N—CH—CH—Ph), 26.59 (N—CH$_3$), 2.39 (Si(CH$_3$)$_3$).

IR (CDCl$_3$): 1742 cm$^{-1}$.

EXAMPLE VIII

Synthesis of 1-methyl-3-(2,2,5,5-tetramethyl-1-aza-2,5-disilacyclopentyl)-4-phenyl-2-azetidinone employing diethyl aluminum chloride as metal source 10 mmoles of n-butyllithium (6.67 ml of a 1.5 molar solution in hexane) was added to a stirred solution containing diisopropylamine (1.40 ml; 10 mmoles) and 25 ml of diethyl ether at −70° C. This reaction mixture was stirred for 10 min and then 2,2,5,5-tetramethyl-1-aza-2,5-disilacyclopentane-1-acetic acid ethyl ester (2.45 g; 10 mmoles) was added. The solution was stirred for another 15 min at −70° C. and then 20 mmoles of diethyl aluminum chloride (20.00 ml of a 1.0 molar solution in hexane) was added. Immediately a white solid began to precipitate. Then N-(benzylidene)methylamine (1.19 g; 10 mmoles) was added. The reaction mixture was stirred for another 15 min at −70° C. and after being warmed up to room temperature quenched with 20 ml of a saturated aqueous ammonium chloride solution. A vigorous evolution of ethane occurred. The water layer was extracted with diethyl ether. The diethyl ether extract was washed with water, dried with sodium sulfate and concentrated in vacuo to give 2.86 g (90%) of the pure 2-azetidinone product as a pale yellow solid with the same physical data as the product obtained in example VIA. The $^1$H NMR spectrum revealed that the product was a mixture of cis- and trans-isomers (cis/trans ratio 10:90).

EXAMPLE IX

Synthesis of an enantiomerically enriched trans-1-methyl-3-diethylamino-4-phenyl-2-azetidinone 13.33 ml of 1.5 molar n-butyllithium in hexane, equivalent to 20 mmoles n-butyllithium, was added to a solution of 2.02 g (20 mmoles) of diisopropylamine in 25 ml benzene. The resulting solution of lithium diisopropylamide was stirred for 10 min. Then 3.18 g (20 mmoles) of the corresponding enantiomerically pure N,N-diethylglycine menthyl ester was added causing an exothermic reaction. The resulting solution was stirred for 30 min. Then a solution of 2.73 g (20 mmoles) of zinc dichloride in 20 ml of diethyl ether was added resulting in a yellow solution. This solution was stirred for 10 min. Most of the diethyl ether and hexane present in solution was evaporated in vacuo. 2.38 g (20 mmoles) of N-(benzylidene)methylamine was added to the resulting benzene solution and the reaction mixture refluxed for 70 min. During this period some solid material precipitated. The reaction mixture was cooled down to room temperature and diluted with 20 ml of diethyl ether. 15 ml of a saturated aqueous ammonium chloride solution was added to the reaction mixture. The organic phase was separated and was washed twice with 15 ml portions of a saturated aqueous ammonium chloride solution and twice with 15 ml portions of water. The organic phase was extracted with 2 portions of 20 ml 4 molar HCl solution in water. The acidic aqueous phase was washed 3 times with 20 ml portions of diethyl ether. The aqueous phase was made basic with a concentrated ammonia solution and extracted with three 20 ml portions of diethyl ether. The organic extract was dried with sodium sulfate and concentrated in vacuo yielding 3.5 g (75%) of the 2-azetidinone as a white solid, with the same properties as those given for example IIA.

$^1$H NMR (60 MHz, CDCl$_3$) in the presence of an optically active paramagnetic shift reagens (Eu(TFC)$_3$) showed the presence of two resonances for H3 of the two enantiomers at 5.30 and 5.50 ppm respectively in a 1:2 ratio, thus indicating an enantiomeric excess of 33%. Under the same conditions for the 2-azetidinone obtained in example IIA the ratio of these resonances was 1:1.

Experiment without the additional metal compound.

An etheral solution of the lithium enolate of 2,2,5,5-tetramethyl-1-aza-2,5-disilacyclopentane-1-acetic acid ethyl ester was prepared as described in Example VI at $-70°$ C. In contrast to the procedure followed in Example VI a metal compound (with the formula MW(X)$_a$(Y)$_b$(Z)$_c$ with M, P, W, Y, Z, a, b and c are as defined above) was not added and the lithium enolate in 25 ml of diethyl ether was directly reacted further with N-(benzylidene)methylamine (1.19 g; 10 mmoles) at $-70°$ C. After 2 hours stirring at $-70°$ C. no formation of the $\beta$-lactam could be detected using $^1$H NMR.

We claim:

1. A compound of the formula

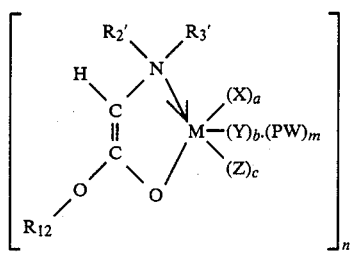

wherein R$_{12}$ is selected from the group consisting of alkyl, aryl and aralkyl, each unsubstituted or substituted with alkyl, aryl or aralkyl, M is selected from the group consisting of zinc, aluminum, zirconium, boron, tin and titanium, P is alkali metal, X, Y and Z are individually selected from the group consisting of alkyl, aryl and alkoxide, W is selected from the group consisting of thiolate, and triflate, and a,b,c and m are 0 or 1 with at least one being 1, n=1-6, all being integers, R$_2'$ and R$_3'$ are individually selected from the group consisting of hydrogen, alkyl, aryl and aralkyl, each unsubstituted or substituted with alkyl, aryl, or aralkyl or

wherein R$_6$, R$_7$ and R$_8$ are individually selected from the group consisting of alkyl, aryl and aralkyl, R$_2'$ and R$_3'$ together with the nitrogen atom to which they are attached form a ring of formula III

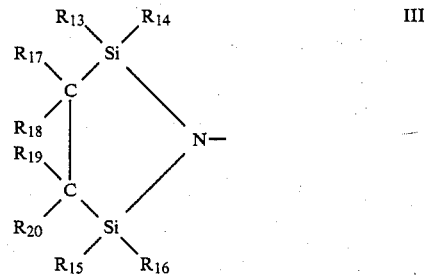

wherein R$_{13}$, R$_{14}$, R$_{15}$, R$_{16}$, R$_{17}$, R$_{18}$, R$_{19}$ and R$_{20}$ are individually selected from the group consisting of alkyl, aryl and aralkyl.

2. A compound according to claim 1, wherein M is zinc.

3. Compound according to claim 1 wherein
R$_2$ and R$_3$ are each ethyl,
M is zinc,
X and Y are ethyl,
P is lithium,
W is chloride,
n is 2 and m=1.

* * * * *